(12) United States Patent
Qin et al.

(10) Patent No.: US 8,889,342 B2
(45) Date of Patent: Nov. 18, 2014

(54) AZIDE FUNCTIONALIZED POLY(3-HEXYLTHIOPHENE) AND METHODS OF FORMING SAME

(71) Applicant: Brookhaven Science Associates, LLC, Upton, NY (US)

(72) Inventors: Yang Qin, Albuquerque, NM (US); Robert B. Grubbs, Miller Place, NY (US); Young Suk Park, Torrance, CA (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 14/174,526

(22) Filed: Feb. 6, 2014

(65) Prior Publication Data

US 2014/0284568 A1   Sep. 25, 2014

Related U.S. Application Data

(62) Division of application No. 13/194,151, filed on Jul. 29, 2011, now Pat. No. 8,679,730.

(60) Provisional application No. 61/369,342, filed on Jul. 30, 2010.

(51) Int. Cl.
  *B82Y 10/00*   (2011.01)
  *B82Y 40/00*   (2011.01)
  *C08G 75/06*   (2006.01)

(52) U.S. Cl.
  USPC ............ 430/319; 427/521; 525/474; 528/14; 528/20; 528/27; 549/4

(58) Field of Classification Search
  None
  See application file for complete search history.

(56) References Cited

PUBLICATIONS

Choi et al., 2010, caplus an 2010:93581.*

* cited by examiner

*Primary Examiner* — Sun Jae Yoo
(74) *Attorney, Agent, or Firm* — Dorene M. Price; Lars O. Husebo

(57) ABSTRACT

This disclosure relates to a polymer having the formula:

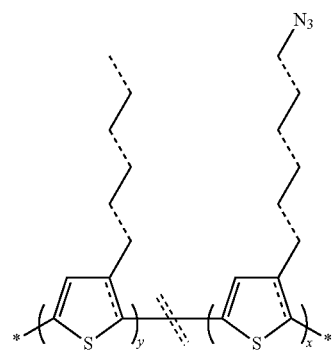

wherein x is between 1 and about 100 an y is between about 99 and about 1, and x+Y=about 100. The disclosure also includes the use of the polymer in photovoltaic devices.

4 Claims, 14 Drawing Sheets

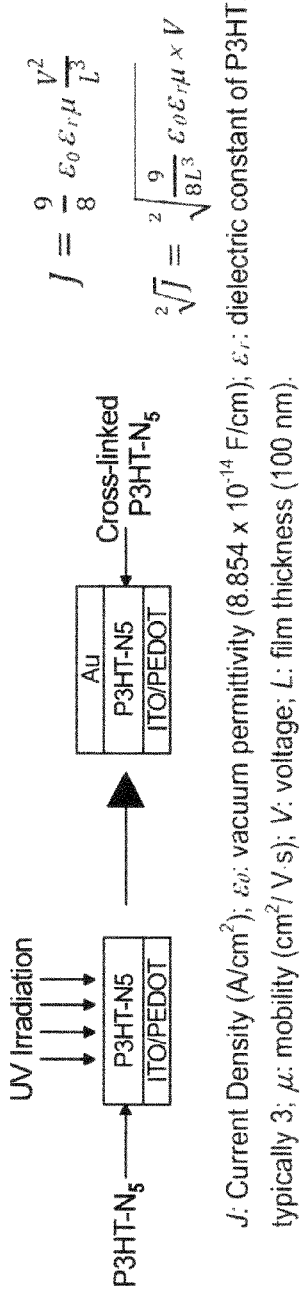
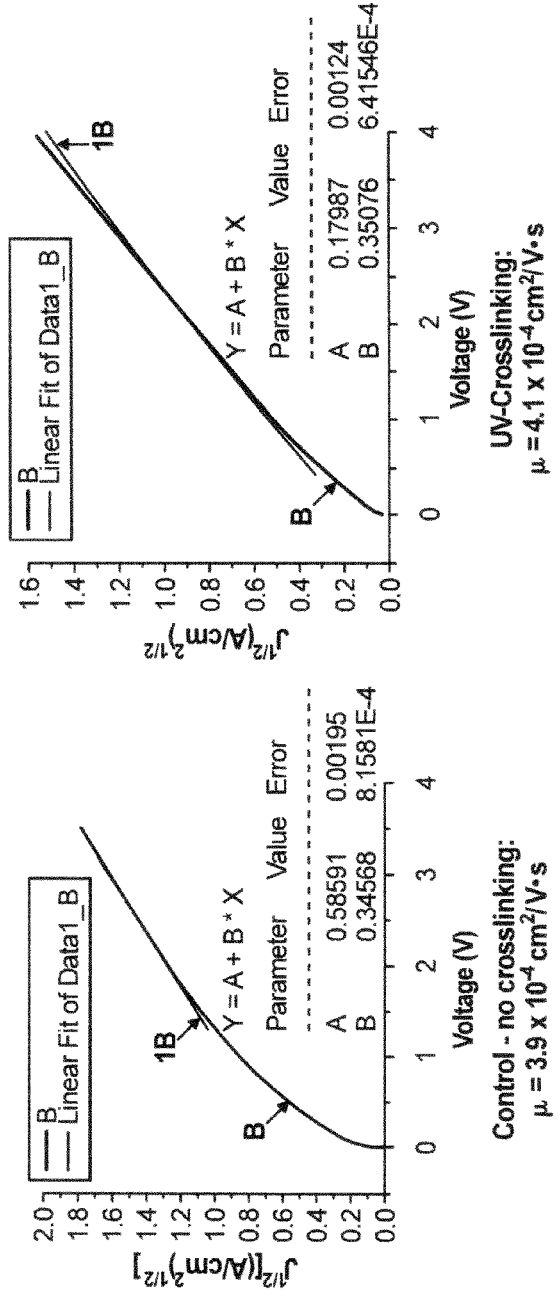
$J = \frac{9}{8}\varepsilon_0\varepsilon_r\mu\frac{V^2}{L^3}$
$\sqrt[2]{J} = \sqrt[2]{\frac{9}{8L^3}\varepsilon_0\varepsilon_r\mu} \times V$
*J*: Current Density (A/cm²); $\varepsilon_0$: vacuum permittivity (8.854 × 10⁻¹⁴ F/cm); $\varepsilon_r$: dielectric constant of P3HT, typically 3; $\mu$: mobility (cm²/V·s); *V*: voltage; *L*: film thickness (100 nm).
Fig. 10
Charge Mobility Measurements Performance of Imprinted Devices

| Polymer | GISAXS a(backbone) | b (π-π) | Hole Mobility μ(cm₂/V s) |
|---|---|---|---|
| P3HT† | 16 Å | 3.8 Å | ~10⁻⁵ - 10⁻⁴ |
| P3HT-N5 | 16.2 Å | 3.6 Å | 3.9 x 10⁻⁴ |
| P3HT-N5 (crosslinked) | 15.9 Å | 3.7 Å | 4.1 x 10⁻⁴ |

†P3HT spacing data from doi: 10.1002/adma.200501838

AZIDE FUNCTIONALIZED POLY(3-HEXYLTHIOPHENE) AND METHODS OF FORMING SAME

CROSS REFERENCES TO RELATED APPLICATIONS

This application is a divisional application of U.S. patent application Ser. No. 13/194,151 filed Jul. 29, 2011, which claims priority under U.S.C. 119(e) to U.S. Provisional Application Ser. No. 61/369,342 filed Jul. 30, 2010, the contents of each of which are incorporated herein by reference in its entirety.

STATEMENT OF GOVERNMENT RIGHTS

This invention was made with Government support under contract number DE-AC02-98CH10886, awarded by the U.S. Department of Energy. The Government has certain rights in the invention

FIELD OF INVENTION

The invention relates to the field of organic conducting polymers. The invention also relates to methods of fabricating organic monomers and conducting polymers, methods of rendering conducting polymers insoluble, and methods of using soluble and insoluble conducting polymers.

BACKGROUND

Organic electronic devices employing semi-crystalline organic semiconducting polymers, e.g., poly(3-hexylthiophene) (P3HT), have great potential for low cost and large throughput production. Performance of these devices depends strongly on the morphologies of the constituting organic components whose optical and electrical on the morphologies of the constituting organic components whose optical and electrical properties rely on the degree of crystallinity. Small changes in the internal structures, i.e., packing/orientation of polymeric chains and morphologies on the nanometer scale, can have a large influence on device operation in organic electronic devices. Stabilizing these materials and morphologies without significantly changing their favorable properties, either to ensure long-term performance or for further processing of more complex device architectures, presents a significant challenge. One of the methods of solving this challenge is to crosslink the semiconducting polymers, locking in favorable morphologies and nanostructures. Polythiophenes are among the most commonly applied polymers in organic photovoltaic devices. In organic light-emitting diode (OLED)-based devices, many other organic molecules/polymers are more common One previously demonstrated approach to stabilizing polythiophenes incorporates functional groups that crosslink through reaction with one another, e.g., oxetane groups. This necessitates a high concentration of functional monomer and alters the polymer structure, and thus the optical and electronic properties. Others have used more reactive cross-linkers that are less likely to impact structure but introduce species potentially detrimental to polymer properties. Two recent examples demonstrate UV crosslinking of polythiophenes with fluoroarylazide groups, which can act as electron traps, and alkyl halides, which introduce halide-functional byproducts. This group has successfully stabilized P3HT using a thermally-initiated peroxide crosslinking method in exploring experimental routes to patterning organic semiconductors, in which a large concentration of peroxides had to be applied leading to dilution of P3HT and thus decreased light absorption.

SUMMARY

Recognizing the challenges of obtaining stabilized organic semiconductors without compromising their optical, electrical, or structural properties, a method of synthesizing UV-crosslinkable azide-functionalized P3HT polymers has been developed. To minimize impact on polymer structure and electronic properties, a chemical synthesis route for crosslinking polythiophene using ultraviolet (UV) light is used. UV-initiated crosslinking decouples the process of film stabilization from thermal treatments that are required to achieve favorable electronic properties. The approach uses azide-functional alkylthiophenes, which are compatible with the polythiophene crystal structure. These can be photolyzed to highly reactive nitrene species to facilitate crosslinking in the polymer alkyl side chains rather than along the polymer backbone whose integrity is linked to performance.

In some embodiments, a thiophene-based monomer, (6-(3-thienyl)hexyloxy)-tert-butyldimethylsilane, was synthesized.

In some embodiments, a thiophene-based monomer, (6-(3-(2,5-dibromothienyl)hexyloxy)-tert-butyldimethylsilane (i.e., "Monomer 1") is synthesized through Grignard coupling reaction followed by bromination using commercially available materials. Monomer 1 may then be mixed with 2,5-dibromo-3-hexylthiophene, a commercially available precursor for the synthesis of P3HT, and subjected to Grignard metathesis (GRIM) polymerization to give the P3HT derivative P3HT-Si$_{mp}$, where "mp" represents the mole percentage of Monomer 1 in the reaction mixture and silylether functionalities in the polymer.

According to one embodiment, the mp can range from about 1 to about 100, and in another embodiment the mp can range from about 1 to about 20, and in yet another embodiment the mp can range from about 2 to about 10. In still another specific embodiment the mp equals 5, i.e., mp=5. In general, the higher the value of mp the greater the speed of crosslinking. At extreme values of mp it is expected that the physical and electrical properties of the polymer may degrade.

In some embodiments, the silylether groups may be deprotected using tetrabutylammonium fluoride to give hydroxy functionalized P3 HT-OH$_5$. In some embodiments, the last step involves converting the hydroxyl groups into azido groups using tetrabutylammonium azide in the presence of triphenylphosphine and 2,3-dichloro-5,6-dicyano-p-benzoquinone, followed by purification using Soxhlet extraction. The final product, P3HT-N$_5$, has a structure similar to previously synthesized P3HT except that 5% of the repeating units bear an azido group at the end of the hexyl side chains and are randomly distributed along the polymer backbone.

The P3HT-N$_5$ was characterized by NMR, GPC, X-ray diffraction. UV-Vis and IR spectroscopy, which showed similar results compared with commercially available P3HTs. The UV-crosslinking behavior of P3HT-N$_5$ was carefully studied. At first, a thin film of P3HT-N$_5$ was exposed to UV irradiation leading to an insoluble semiconducting film. The disappearance of the azido groups, which upon UV irradiation releases volatile N$_2$ gas as the only byproduct, was confirmed by IR spectroscopy. More interestingly, the morphologies and optical and electronic properties of the polymer film remained unchanged after crosslinking, as confirmed by X-ray diffraction, UV-Vis spectroscopy, and charge mobility/

OPV cell measurements, respectively. To further demonstrate the utility of the method, a P3HT-N$_5$ film was patterned with sub-100-nm features using a nano-stamping strategy followed by UV irradiation. The resulting micro-structured polymer film was robust enough, as confirmed by SEM measurements, to withstand later solution processes for building more complex structures including the bulk heterojunction (BHJ) morphology for organic photovoltaics (OPVs) which is commonly thought to significantly improve OPV performances.

In some embodiments, the loading percentage of the azido groups can be fine-tuned by varying the reaction ratios of Monomer 1 and 2,5-dibromo-3-hexylthiophene.

In some embodiments, molecular weights of the final product can be controlled and fine-tuned by varying the amount of catalyst used in the GRIM polymerization.

In some embodiments, upon UV-crosslinking, the azido groups preferentially attack alkyl chains and the byproduct is N$_2$, which can be easily removed, ensuring minimum impact on the physical properties of the organic semiconductors.

The method is general and can be applied to other semiconducting polymers by coupling Monomer 1 with other dibromo-alkyl monomers to synthesize new hybridized polymers or simply UV irradiating a mixture of P3HT-N$_{mp}$ and other alkyl-bearing polymers. Since almost all polymers used in organic electronic devices have alkyl side chains as solubilizing groups, the methodology can in principle be expanded to any other system and have great potential in the field of organic electronics.

This method is applicable to other nanotechnologies for fabricating robust and microstructured semiconductors, e.g., step-and-flash nanoimprinting, UV lithography, and laser interference lithography.

According to one embodiment, a novel chemical compound (11) is disclosed. The compound has the following formula:

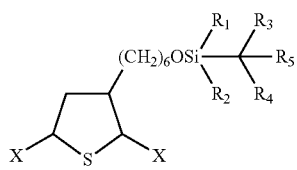

(11)

The R groups, i.e., R$_1$, R$_2$, R$_3$, R$_4$, and R$_5$, of compound (11) are functional groups, while X is a halogen.

According to another embodiment, a novel polymer (13) is disclosed. The polymer has the following formula:

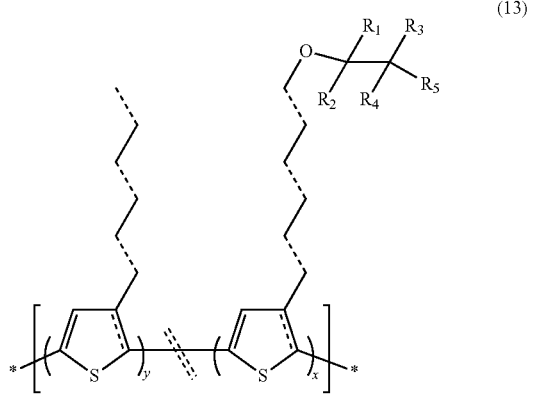

(13)

The R groups, i.e., R$_1$, R$_2$, R$_3$, R$_4$, and R$_5$, of polymer (13) are functional groups. The reference "x" of polymer (13) is between 1 and about 100, "y" is between about 99 and 0, and x+y equals about 100.

According to still another embodiment, a chemical compound (10) having the formula below is disclosed.

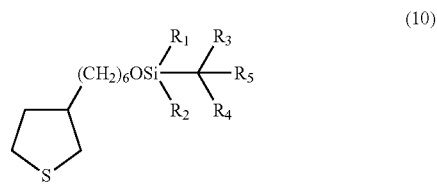

(10)

The R groups, i.e., R$_1$, R$_2$, R$_3$, R$_4$, and R$_5$, of chemical compound (10) are functional groups.

According to yet another embodiment, a polymer (15) having the following formula is disclosed.

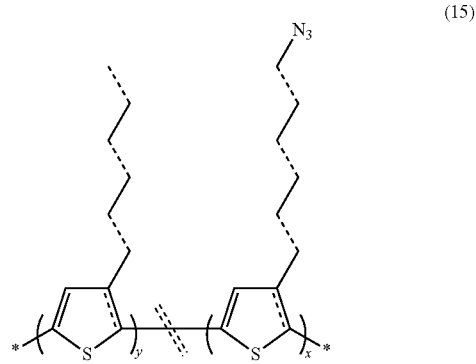

(15)

The reference "x" of polymer (15) is between 1 and about 100, "y" is between about 99 and 0, and x+y equals about 100.

It should be understood that the foregoing, being a summary, is necessarily a brief description of some aspects of the invention, which may be better understood with reference to the drawings and the following detailed description.

BRIEF DESCRIPTION OF THE DRAWINGS

As is common practice in the art, the following figures may not be drawn to scale. Schematic depictions are used to emphasize the particular features of the invention and as a reference for their description.

FIG. 10 presents the mathematical equations used to provide the charge mobility measurements and graphical illustrations of the charge mobility measurements utilizing the actual and extrapolated data of non-crosslinked P3HT-N$_5$ and UV-crosslinked P3HT-N$_5$, respectively.

DETAILED DESCRIPTION

Recognizing the challenges of obtaining stabilized organic semiconductors without compromising their optical, electrical, or structural properties, a method of synthesizing UV-crosslinkable azido-functionalized P3HT polymers has been developed. To minimize impact on polymer structure and electronic properties, a chemical synthesis route for crosslinking polythiophene using UV light is used. UV-initiated cross-linking decouples the process of film stabilization from thermal treatments that are required to achieve favorable electronic properties. The approach uses azide-functionalized alkylthiophenes, which are compatible with the polythiophene crystal structure. These can be photolyzed to highly reactive nitrene species to facilitate crosslinking in the polymer alkyl side chains rather than along the polymer backbone the integrity of which is critical for performance.

While the following examples are explained with reference to specific amounts and ratios of starting materials, intermediates, and final products, it is to be understood that the method is not limited to these specific parameters. In fact, the method is quite general and adaptable. For example, the loading percentage of the azido groups can be fine-tuned by varying the reaction ratios of Monomer 1 and 2,5-dibromo-3-hexylthiophene. Molecular weights of the final product can be controlled and fine-tuned by varying the amount of catalyst used in the GRIM polymerization. Upon UV-crosslinking, the azido groups preferentially attack alkyl chains and the byproduct is N$_2$, which can be easily removed, ensuring minimum impact on the physical properties of the organic semiconductors.

The method is general and can be applied to other semiconducting polymers by coupling Monomer 1 with other dibromo-alkyl monomers to synthesize new hybridized polymers or simply UV irradiating a mixture of P3HT-N$_{mp}$ and other alkyl-bearing polymers. Since almost all polymers used in organic electronic devices have alkyl side chains as solubilizing groups, the methodology can in principle be expanded to any other system and have great potential in the field of organic electronics.

This method is applicable to other nanotechnologies for fabricating robust and microstructured semiconductors, e.g., step-and-flash nanoimprinting, UV lithography, and laser interference lithography.

Example 1

Figure 1:
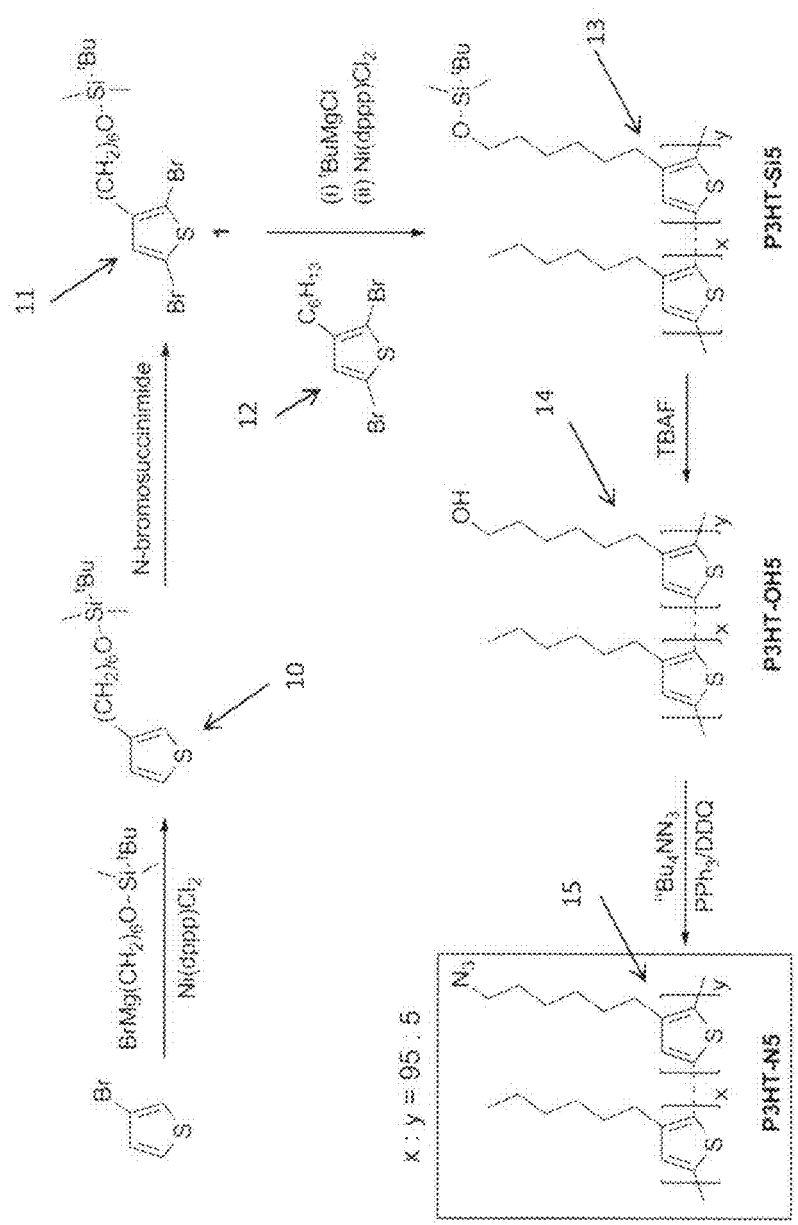
FIG. 1 is a schematic diagram depicting the reaction path to synthesize Monomer 1 and convert it to P3HT-N$_{mp}$.

In this example, a thiophene-based monomer, (6-(3-thienyl)hexyloxy)-tert-butyldimethylsilane 10, as shown in FIG. 1, was first synthesized through Grignard coupling reaction followed by bromination using commercially available materials to produce (6-(3-(2,5-dibromothienyl)hexyloxy))-tert-butyldimethylsilane 11 (i.e., Monomer 1) as shown in FIG. 1. Monomer 1 was then mixed with 2,5-dibromo-3-hexylthiophene 12, a commercially available precursor for the synthesis of P3HT, and subjected to Grignard metathesis (GRIM) polymerization. i.e., tert-butylMgCl and Ni(dppp)Cl$_2$, to give P3HT derivative P3HT-Si$_{mp}$ 13, as shown in FIG. 1, where "mp" represents the mole percentage of Monomer 1 in the reaction mixture and silylether functionalities in the polymer. In the present example, mp=5. The silylether groups were deprotected using tetrabutylammonium fluoride (TBAF) to give hydroxy-functionalized P3HT-OH$_5$ (P3HT-OH$_{mp}$ 14, as shown in FIG. 1). The last step involved converting the hydroxyl groups into azido groups using tetrabutylammonium azide (Bu$_4$NN$_3$) in the presence of triphenylphosphine (PPh$_3$) and 2,3-dichloro-5,6-dicyano-p-benzoquinone (DDQ), followed by purification using Soxhlet extraction. The final product, P3HT-N$_5$ (P3HT-N$_{mp}$ 15, where x:y=95:5, as shown in FIG. 1), has a structure similar to previously synthesized P3HT except that five percent (5%) of the repeating units bear an azido group at the end of the hexyl side chains and are randomly distributed along the polymer backbone and x is between 1 and about 100 an y is between about 99 and about 1.

The P3HT-N$_5$ was characterized by NMR, GPC, X-ray diffraction, UV-Vis and IR spectroscopy, which showed similar results compared with commercially available P3HTs. The UV-crosslinking behavior of P3HT-N$_5$ was studied. At first, a thin film of P3HT-N$_5$ was exposed to UV irradiation leading to an insoluble semiconducting film. The disappearance of the azido groups, which upon UV irradiation release volatile N$_2$ gas as the only byproduct, was confirmed by IR spectroscopy. More interestingly, the morphologies and optical and electronic properties of the polymer film remained unchanged alter crosslinking, as confirmed by X-ray diffraction, UV-Vis spectroscopy, and charge mobility/OPV cell measurements, respectively.

Detailed Synthetic Procedure for Example 1

Synthesis of the intermediate, (6-(3-thienyl)hexyloxy)-tert-butyldimethylsilane, proceeded as follows. To a suspension of Mg (4.3 g, 0.18 mol) in 200 ml tetrahydrofuran (THF) was added slowly (6-bromohexyloxy)-tert-butyldimethylsilane (26.3 g, 0.089 mol) while maintaining the temperature below 60° C. The reaction mixture was stirred at 60° C. for 2 hour and then transferred at 0° C. to another Schlenk flask containing 3-bromothiophene (15.3 g, 0.094 mol) and [1,3-bis(diphenylphosphinio)propane]dichloronnickel(II) (1.0 g, 1.85 mmol) in 100 mL THF. The mixture was then warmed to room temperature and stirred overnight. The reaction mixture was poured into 500 mL ice water and the aqueous phase was extracted with ether three times. The combined organic phase was washed with water and brine, and volatile solvents were removed under reduced pressure. After this standard aqueous workup, the product was isolated by vacuum distillation (0.3 torr, 99-101° C.) as a colorless liquid (20.4 g, 77% yield). $^1$H NMR (400.132 MHz, CDCl$_3$): δ=7.25, 6.93 (m, 3H, aromatic H's), 3.60 (t, 2H, —SiOCH$_2$—), 2.63 (t, 2H, ThCH$_2$—), 1.64-1.35 (m, 8H, ThCH$_2$(CH$_2$)CH$_2$OSi), 0.90 (s, 9H, tert-butyl H's), 0.05 (s, 6H, Si(CH$_3$)$_2$).

Synthesis of a monomer, (6-(3-(2,5-dibromothienyl)hexyloxy))-tert-butyldimethylsilane 11 (Monomer 1), as shown in FIG. 1, proceeded as follows, (6-(3-thienyl)hexyloxy)-tert-butyldimethylsilane 10 (FIG. 1) (20.4 g, 0.068 mmol), was dissolved in 250 mL N,N-dimethylformamide (DMF) and cooled to 0° C. N-bromosuccinimide (24.9 g, (0.14 mol) was added in one portion and the mixture was slowly warmed to room temperature and stirred overnight. After standard aqueous workup (see description above), the product was isolated by vacuum distillation (30 mTorr, 111-113° C.) as a slightly yellow liquid (18.3 g, 59% yield). $^1$H NMR (400.132 MHz, CDCl$_3$): δ=6.79 (s, 1H, Th—H4), 3.62 (t, 2H, —SiOCH$_2$—), 2.54 (t, 2H, ThCH$_2$—), 1.57-1.34 (m, 8H, ThCH$_2$(CH$_2$)$_4$CH$_2$OSi), 0.91 (s, 9H, tert-butyl H's), 0.05 (s, 6H, Si(CH$_3$)$_2$).

Synthesis of P3HT-Si$_5$ (P3HT-Si$_{mp}$ (13), shown in FIG. 1), proceeded as follows, 2,5-Dibromo-3-hexylthiophene (4.95 g, 15.18 mmol) (12 shown in FIG. 1 (15)), and (6-(3-(2,5-dibromothienyl)hexyloxy)-tert-butyldimethylsilane 11, shown in FIG. 1) (0.37 g, 0.80 mmol) were dissolved in 150 mL THF under Argon gas (AR) and tert-butylmagnesium chloride (16.0 mL, 16.0 mmol) was added through a syringe. The mixture was refluxed for 2 h and cannula transferred to another Schlenk flask containing [1,3-bis(diphenylphosphino)propane]dichloronickel(II) (87 mg, 0.16 mmol) cooled to 0° C. The mixture was warmed to room temperature and stirred overnight. The red solution was concentrated under vacuum and precipitated into) a large excess of methanol. After filtration, the solid was Soxhlet extracted with acetone. THF, and CHCl$_3$ for 24 h, respectively, and P3HT-Si$_5$ was isolated by combining and concentrating the THF and CHCl$_3$ fractions followed by precipitation into methanol and dried under vacuum as a black solid (1.43 g, 52% yield). $^1$H NMR (400.132 MHz, CDCl$_3$): δ=6.99 (1H, Th—H4), 3.63 (0.1H, —SiOCH$_2$—), 2.82 (2H, ThCH$_2$—), 1.74-1.23 (8H, ThCH$_2$(CH$_2$)$_4$CH$_2$OSi & ThCH$_2$(CH$_2$)$_4$CH$_3$), 0.93 (3.5H, ThCH$_2$)$_4$CH$_3$ & tert-butyl H's), 0.05 (0.15 H, Si(CH$_3$)$_2$).

Synthesis of P3HT-OH$_5$ 14 (P3HT-OH$_{mp}$, shown in FIG. 1), proceeded as follows. P3HT-Si$_5$ (1.43 g) was dissolved in 20 mL THF at 65° C. and tetrabutylammonium fluoride trihydrate (0.27 g, 0.86 mmol) was added. The mixture was stirred at 65° C. overnight and precipitated into 400 mL methanol and dried at 60° C. under vacuum for 12 h to give P3HT-OH$_5$ as a black solid (1.18 g, 84% yield). $^1$H NMR (400.132 MHz, CDCl$_3$): δ=6.99 (1H, Th—H4), 3.67 (0.1H, CH$_2$OH), 2.82 (2H, ThCH$_2$—), 1.74-1.23 (8H, ThCH$_2$(CH$_2$)$_4$CH$_2$OH & ThCH$_2$(CH$_2$)$_4$CH$_3$), 0.93 (3H, 1.74-1.23 (8H, ThCH$_2$(CH$_2$)$_4$CH$_2$OH & ThCH$_2$(CH$_2$)$_4$CH$_3$), 0.93 (3H, 1.51.

Synthesis of P3HT-N$_5$ 15 (P3HT-N$_{mp}$, shown in FIG. 1), proceeded as follows. Triphenylphosphine (0.092 g, 0.35 mmol) and 2,3-dichloro-5,6-dicyano-p-benzoquinone (DDQ) (0.079 g, 0.35 mmol) were dissolved in approximately 30 mL anhydrous solvent, e.g., THF, and tetrabutylammonium azide (0.10 g, 0.35 mmol) was added as a powder and the resulting mixture was stirred for 5 minutes at room temperature under argon. P3HT-OH$_5$ (0.12 g, 0.042 mmol —OH) was then added and the mixture was stirred at 60° C. under Ar for 1 hour. Then the solution was poured into menthol (100 mL), and a crude product was collected by filtration. The crude P3HT-N$_5$ was further purified by dissolving the crude solid in a minimal amount of THF and precipitating the THF solution into methanol (50 mL). The resulting purified P3HT-N$_5$ was then dried under high vacuum at 60° C. for 12 hours to yield a black powder (0.10 g, 83% yield). $^1$H NMR (400.132 MHz, CDCl$_3$): δ=6.99 (1H, Th—H4), 3.56 (0.1H, CH$_2$N$_3$), 2.82 (2H, ThCH$_2$—), 1.74-1.23 (8H, ThCH$_2$(CH$_2$)$_4$CH$_2$N$_3$ & ThCH$_2$(CH$_2$)$_4$CH$_3$), 0.93 (3H, ThCH$_2$(CH$_2$)$_4$CH$_3$), GPC (CHCl$_3$, 1 mL/min, RI): M$_n$=14.5 kDa, M$_w$=22.7 kDa, PDI=1.57.

Suitable anhydrous solvents may be used in the preparation of the polymer disclosed herein. The anhydrous solvents are preferably those that are safe and least harmful to the environment. According to a preferred embodiment, the anhydrous solvent is tetrahydrofuran.

Example 2

To further demonstrate the utility of the method, a P3HT-N$_5$ film was patterned with sub-100-nm features using a nanostamping strategy followed by UV irradiation. The resulting microstructured polymer film was robust enough, as confirmed by Scanning Electron Microscope (SEM) measurements, to withstand later solution processes for building more complex structures including the bulk heterojunction (BHJ) morphology for organic photovoltaics (OPVs) which is commonly thought to significantly improve OPV performances.

Figure 2:
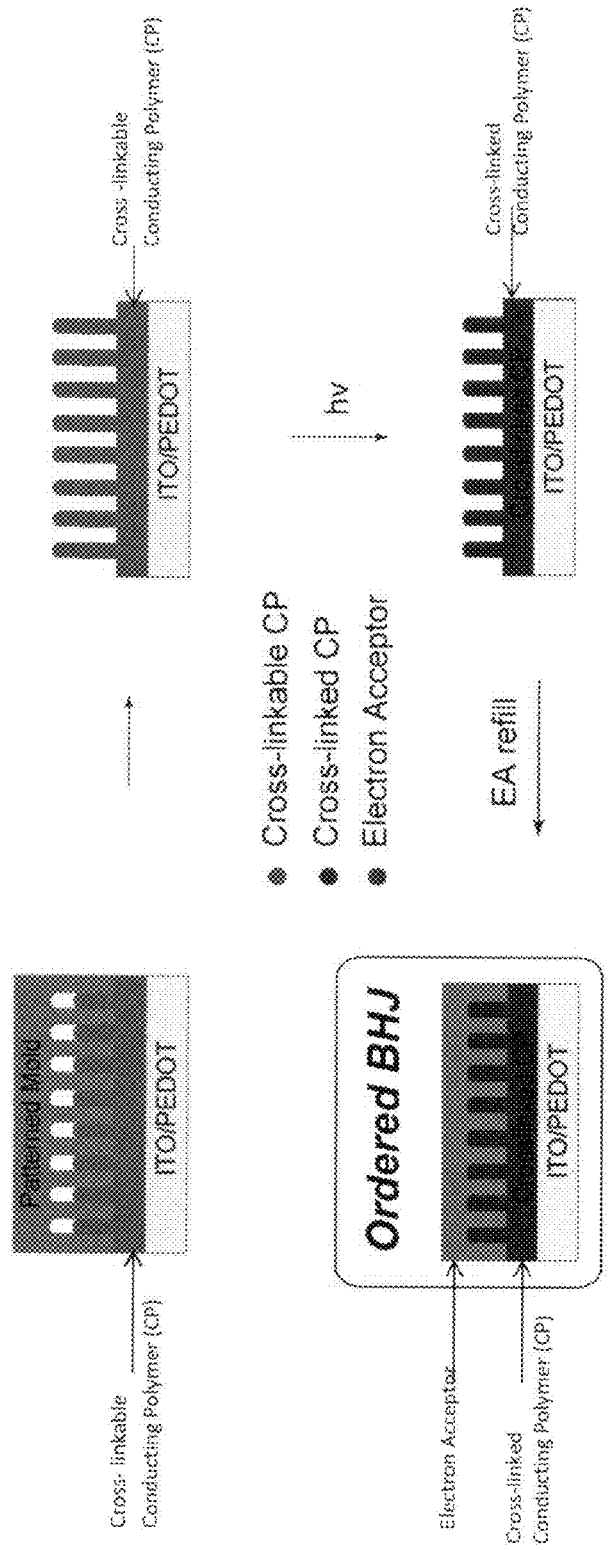
FIG. 2 is a schematic diagram showing a process for using the UV-curable P3HT-N$_{mp}$ to form an ordered bulk heterojunction (BHJ) photovoltaic (PV) structure.

With reference to FIG. 2, a layer of UV-curable conducting polymer is deposited onto a substrate. In this case the immediate substrate is indium tin oxide (ITO) topped with poly(3,4-ethylenedioxythiophene) (PEDOT), but the substrate could be anything compatible with the ultimate structure to be fabricated including silicon, silicon dioxide, silicon nitride, glass, sapphire, metal, etc. A patterned mold is then used to imprint a pattern onto the uncured polymer, here P3HT-N$_5$. The mold is removed, and the imprinted polymer layer subjected to UV light for a time sufficient to cure it, i.e., to crosslink the structure rendering it insoluble in solvents to be used later in the process. Next a layer of electron-accepting (EA) material is deposited onto the patterned crosslinked conducting polymer. In this way an ordered BHJ is formed.

Figure 3:
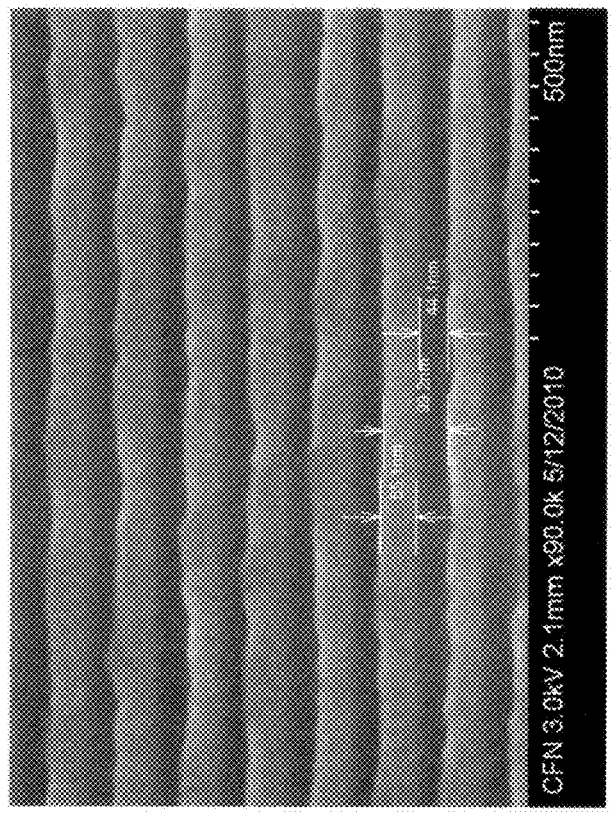
FIG. 3 is a scanning electron micrograph of a layer of imprinted and crosslinked P3HT-N$_5$.

FIG. 3 shows a scanning electron micrograph (SEM) of a layer of imprinted and crosslinked P3HT-N$_5$. Note the approximate 100-nm pitch of ridge-trough units.

Example 3

The ordered BHJ structure of FIG. 2 may also be accomplished by patterning the UV-curable conducting polymer layer using UV lithography.

Figure 4:
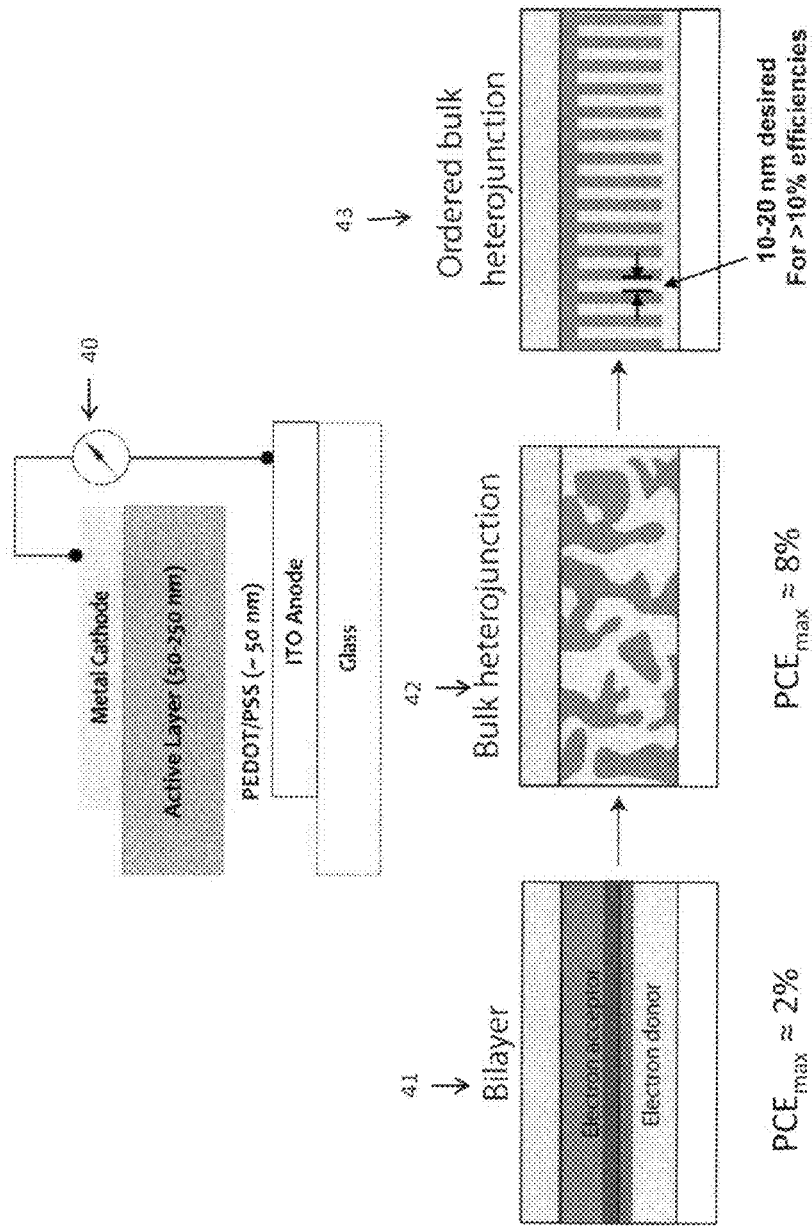
FIG. 4 is a schematic drawing showing the basic structure of a BHJ OPV, a disordered and ordered BHJ.

In FIG. 4, several properties of certain embodiments of the invention are described. Beginning with the basic structure of a BHJ OPV 40 is shown with an indium tin oxide (ITO) anode on glass with a poly (3,4-ethylenedioxythiophene)/poly(styrenesulfonate) (PEDOT/PSS) layer of about 50 nm atop the glass and anode, topped by an active layer ranging in thickness from about 50 to 250 nm, with the structure then capped by a metal cathode. A voltage is produced between the anode and the cathode when the structure is illuminated by photons of a particular wavelength range. Below this diagram are three exemplary morphologies: a bilayer 41 that generally gives a maximum power conversion efficiency ($PCE_{max}$) of about 2%, a BHJ 42 wherein the phases are disordered that has a $PCE_{max}$ of about 8%, and an ordered BHJ 43 having feature sizes on the order of 10-20 nm capable of $PCE_{max}$ greater than 10%. Exciton travel distance in organic material is on the order of 10-20 nm, and thus the morphology of the organic active layer is critical to achieve high performance in OPVs. An ordered BHJ morphology with phase separation on the order of 10-20 nm (as seen in the lower figure (43)) should collect all excitons at the interface and give uninterrupted paths to all separated charges to reach the corresponding electrodes. Strategies for forming such ordered BHJ structures with fine feature sizes include nanopatterning, nanoimprinting, and photolithography, among others.

Figure 5:
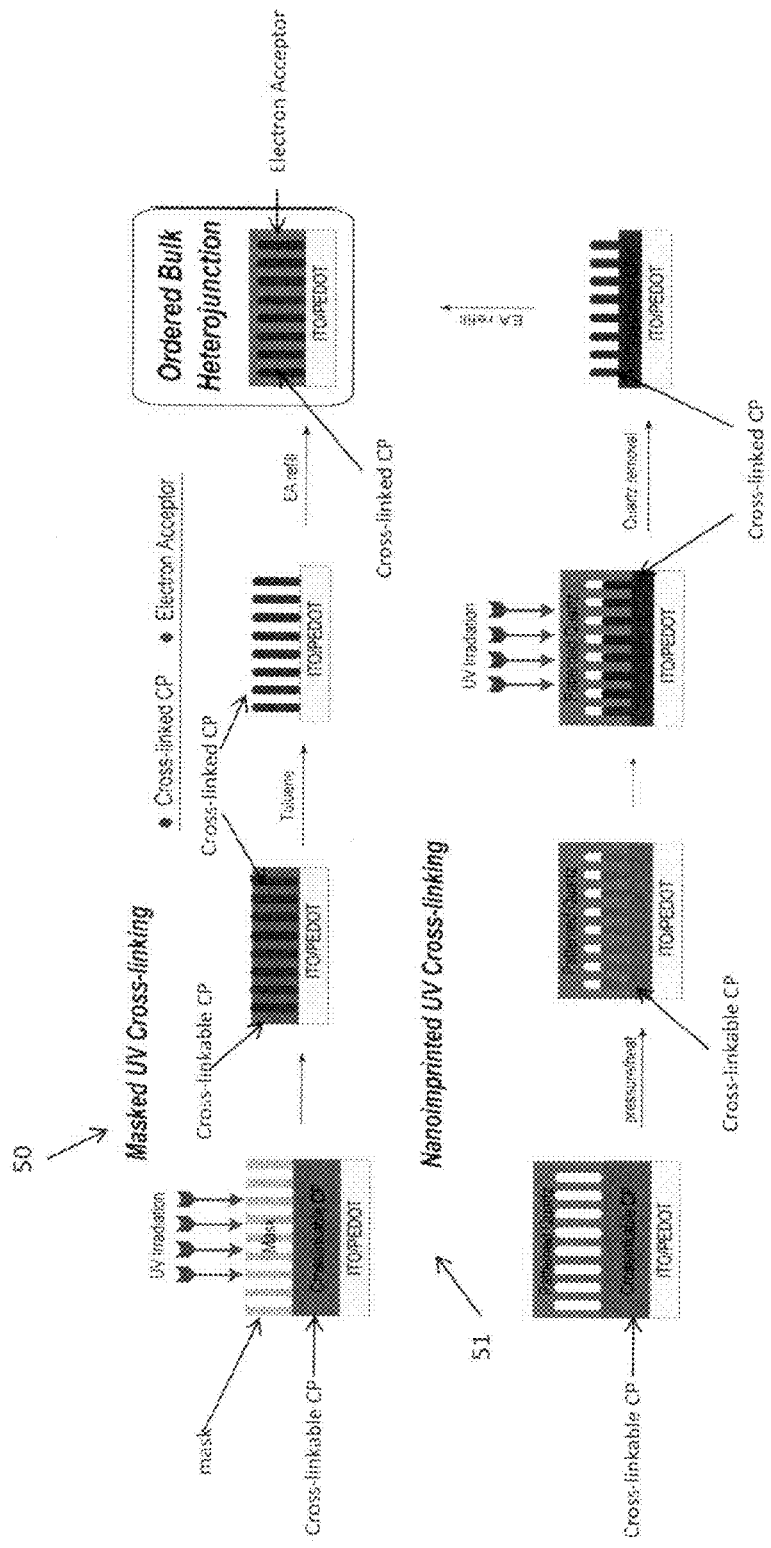
FIG. 5 is a schematic drawing illustrating two processes for fabricating an ordered BHJ, via Masked UV Cross-Linking and Nanoimprinted UV Cross-Linking, respectively.

FIG. 5 illustrates two methods for fabricating an ordered BHJ using the inventive UV-crosslinkable conducting polymer. In the Masked UV Cross-linking process 50, a mask is used to restrict UV exposure to certain parts of the UV-crosslinkable conducting polymer. Upon irradiation, the exposed portion of the conducting polymer crosslinks, becoming insoluble, and the other portion is removed by a solvent such as toluene. An electron-accepting (EA) material is then used to fill in the structure, forming an ordered BHJ. The second process, Nanoimprinted UV Cross-linking 51, uses a nanoimprinting device, such as patterned quartz, to imprint a design into the crosslinkable polymer, here by applying pressure and/or heat. The imprinted conducting polymer is then exposed to UV radiation through the UV-transparent quartz and crosslinks. After the quartz mold is removed, the crosslinked structure is tilled with EA material as before, resulting in an ordered BHJ.

Figure 6:
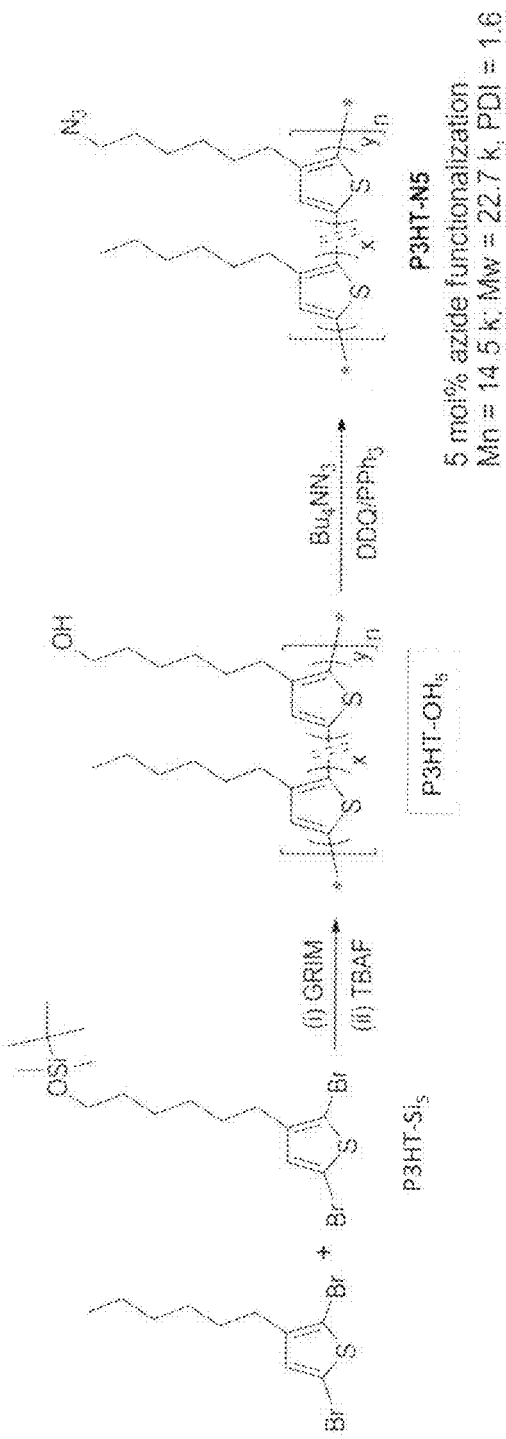
FIG. 6 is a schematic diagram depicting the reaction path to synthesize P3HT-N$_{mp}$.

FIG. 6 illustrates the materials synthesis pathway from $P3HT-Si_5$ to $P3HT-N_5$ via $P3HT-OH_5$.

Figure 7:
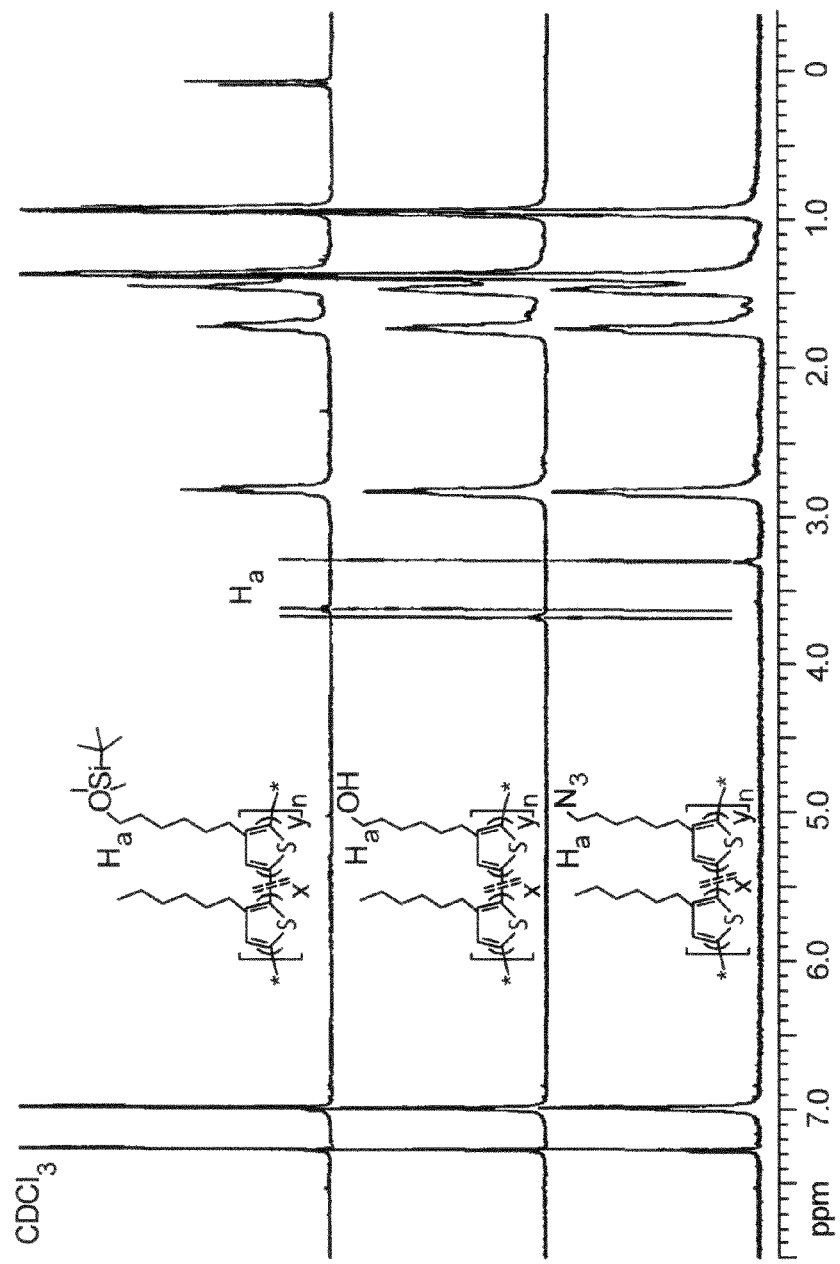
FIG. 7 is a comparative NMR spectra representation of P3HT-Si$_{mp}$, P3HT-OH$_{mp}$, and P3HT-N$_{mp}$, respectively.

FIG. 7 shows NMR spectra corresponding to the three structures. i.e. $P3HT-Si_{mp}$, $P3HT-OH_{mp}$, and $P3HT-N_{mp}$, respectively, indicating that the three compounds differ from each other.

Figure 8:
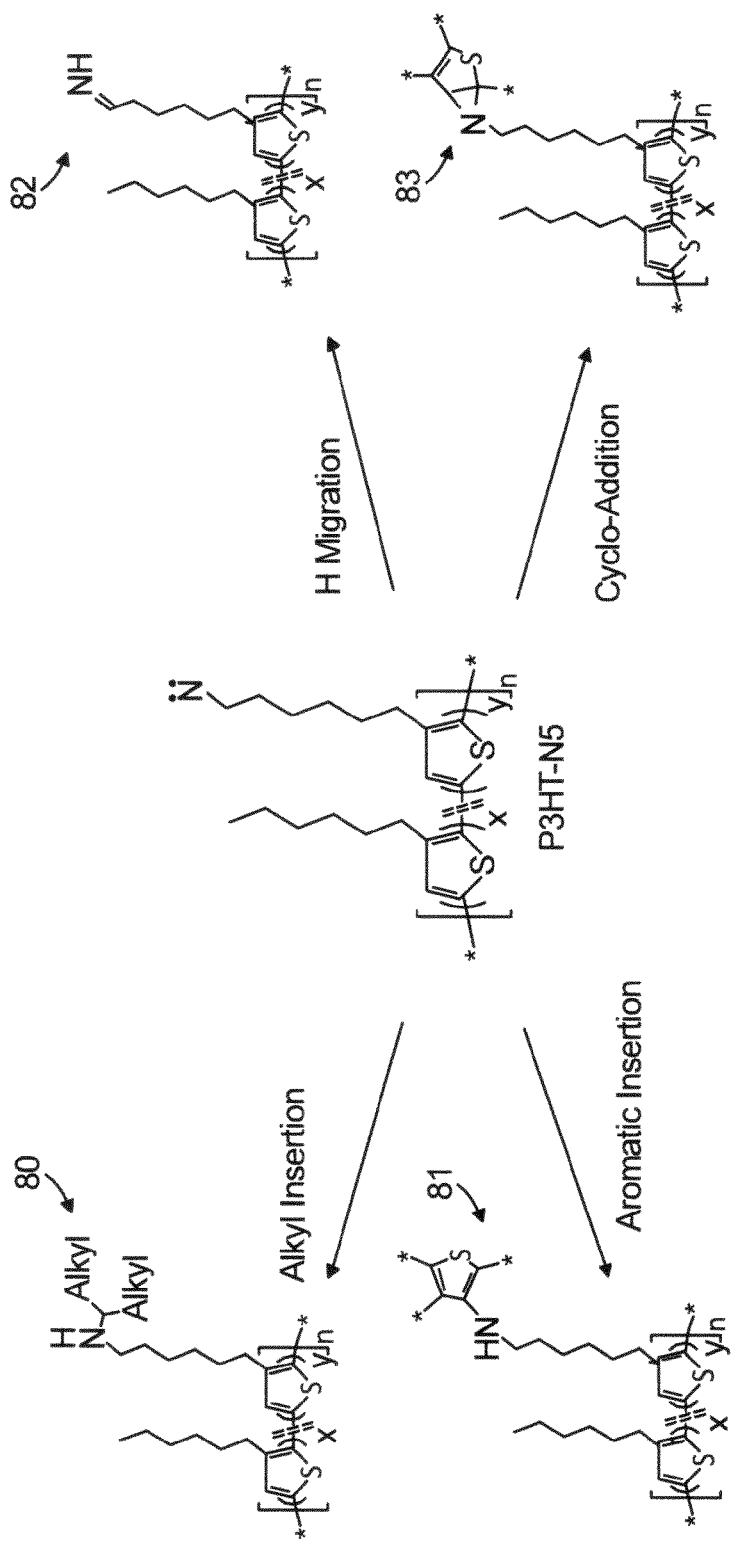
FIG. 8 is a schematic drawing illustrating the disclosed UV-induced cross linking reactions of P3HT-N$_5$.

FIG. 8 illustrates the various UV crosslinking of the $P3Ht-N_{mp}$ Four potential crosslinking pathways involving photogenerated nitrenes are identified: the preferred pathway is insertion of the nitrene into an alkyl C—H bond 80; less preferred pathways include insertion of the nitrene into an aromatic C—H bond 81, intramolecular migration of a hydrogen atom to the nitrene to afford a non-crosslinked imine 82, and cyclo-addition of the nitrene to an aromatic carbon-carbon bond 83.

Figure 9:
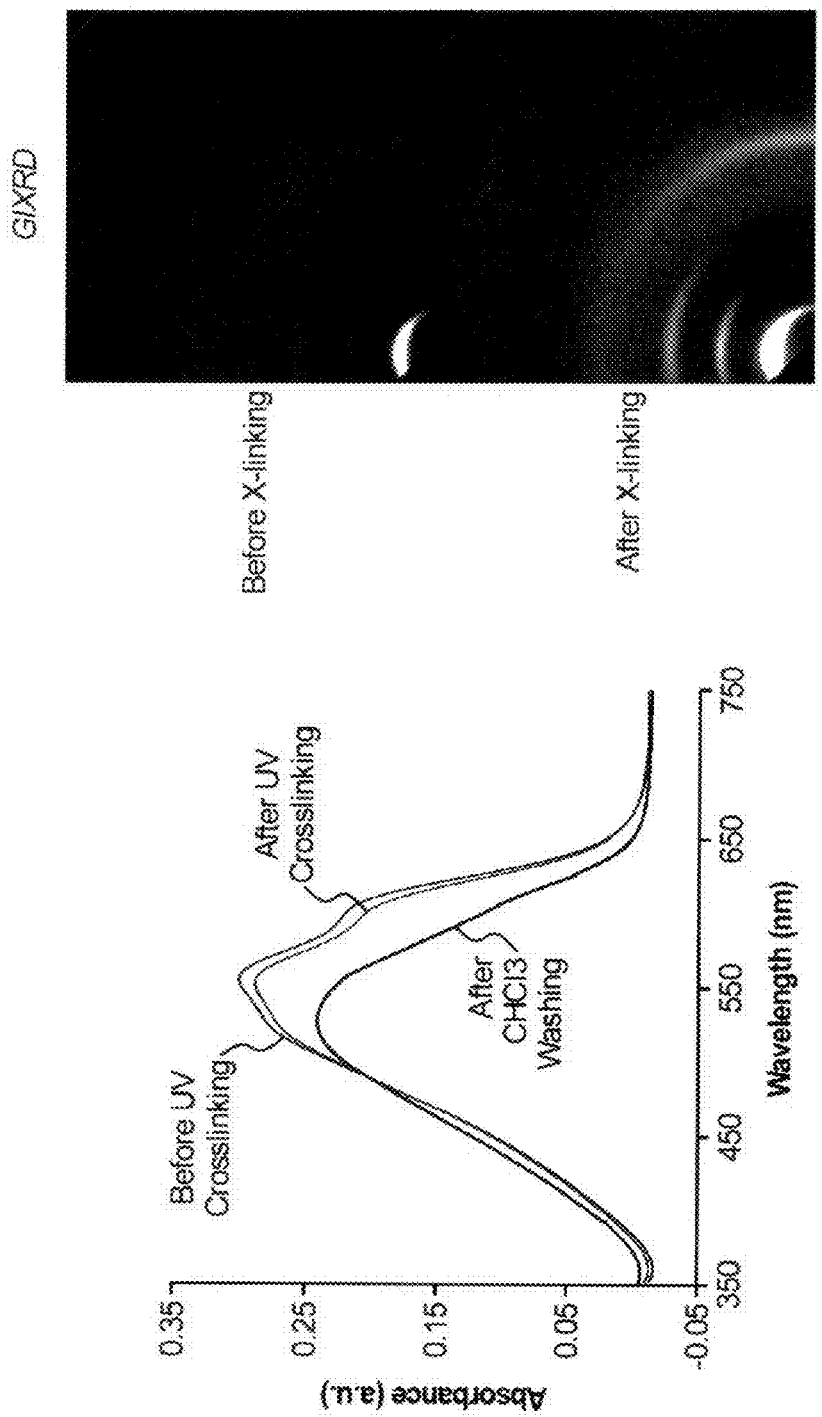
FIG. 9 is a graphical representation of absorption spectrum of the P3HT-N$_5$ polymer film before and after crosslinking, and Grazing Incidence X-Ray Diffraction (GIXRD) patterns taken before and after crosslinking of the P3HT-N$_{mp}$.

FIG. 9 graphically illustrates the ultraviolet-visible (UV-Vis) light absorption spectrum results of cross-linking studies using the $P3HT-N_5$ polymer. The results presented were of the polymer before and after UV crosslinking and are substantially identical. The cross-linked sample was then washed in $CHCl_3$ and compared to the cross-linked and non-cross-linked samples. The resulting curve indicates that removal of a small amount of non-cross-linked polymer decreases the polymer absorbance and results in a decrease in the long-range ordering of the P3HT-N chains. FIG. 9 also shows Grazing Incidence X-Ray Diffraction (GIXRD) patterns taken before and after crosslinking. These patterns show that the structural changes after cross-linking are relatively minor, which is borne out by the small change to the absorption spectrum of a 100-nm film before and after crosslinking. After washing with $CHCl_3$ the film thickness is reduced to about 80 nm and its absorbance concomitantly reduced slightly in the longer wavelengths.

FIG. 10 illustrates charge mobility measurements carried out on non-crosslinked and UV-crosslinked $P3HT-N_5$. The mathematical equations used to provide the charge mobility measurements are presented therein. In order to obtain the measurements non-crosslinked $P3HT-N_5$ was deposited onto ITO/PEDOT and exposed to UV radiation. A gold contact was applied to the cross-linked film and the charge mobility measured. As presented in the UV-Crosslinking graph, cross-linking the film increased the charge mobility slightly.

Figure 11:
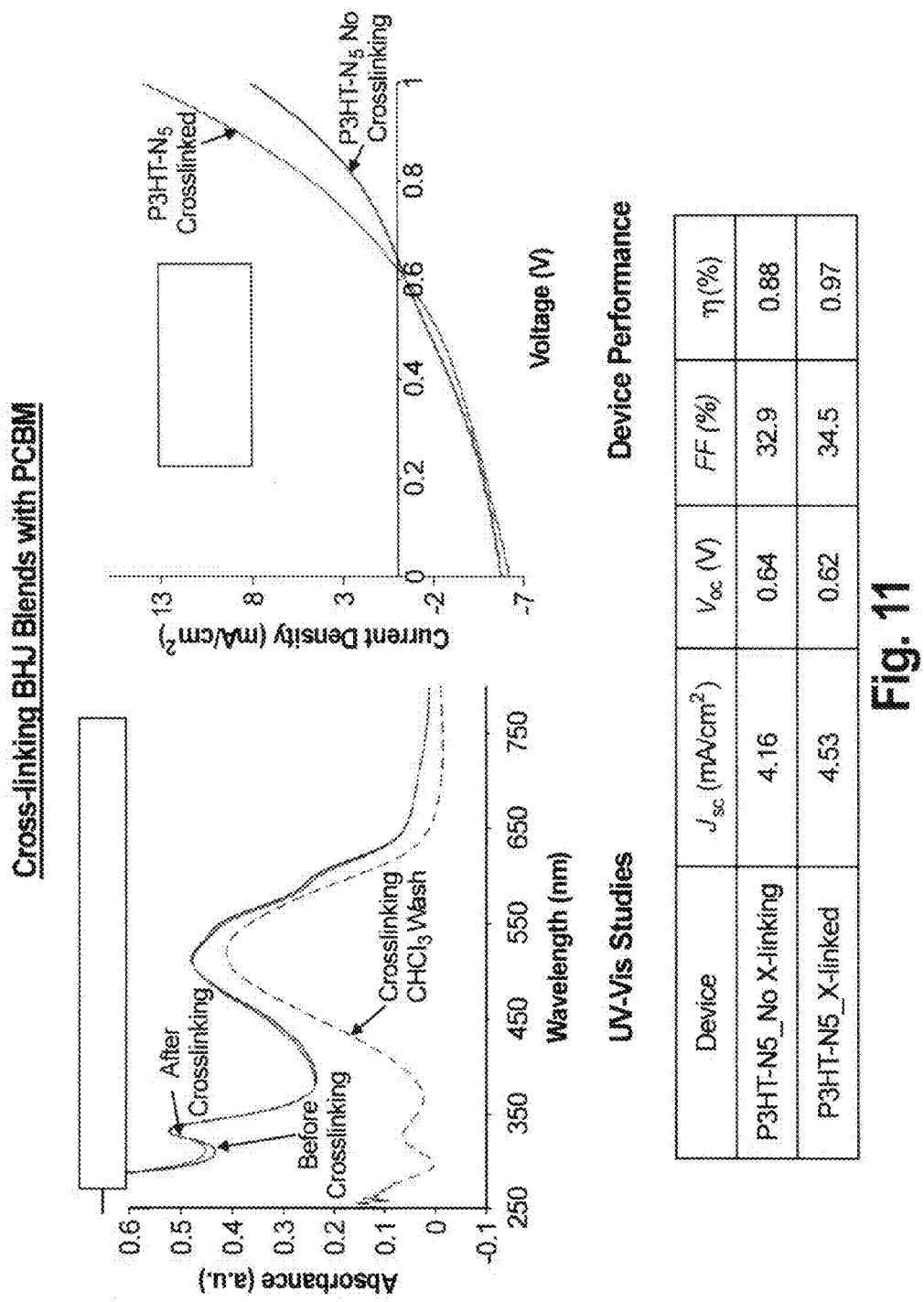
FIG. 11 is a graphical representation of the UV-Vis spectroscopic spectrum of a blend of P3HT-N$_5$ and [6,6]-phenyl-C$_{61}$-butyric acid methyl ester (PCBM), a graphic illustration of current density vs. voltage, and a table presenting the results of non-crosslinking and crosslinking effects on device performance, respectively.

FIG. 11 illustrates UV-vis spectroscopy light absorption results using a blend of the novel $P3HT-N_5$ and [6,6]-phenyl-$C_{61}$-butyric acid methyl ester (PCBM). Two distinct peaks, each corresponding to one of the species, were seen in the UV-Vis spectrum. The spectra taken before and after UV crosslinking are virtually identical. Then the sample was dipped into a solvent that dissolves both non-crosslinked PCBM and $P3HT-N_5$. The resulting dashed curve shows that the UV exposure did, indeed, render the $P3HT-N_5$ insoluble while virtually no PCBM remains after immersion in the solvent. As seen in the graph of current density vs. voltage and the chart below it, crosslinking had no deleterious effect on device performance.

Figure 12:
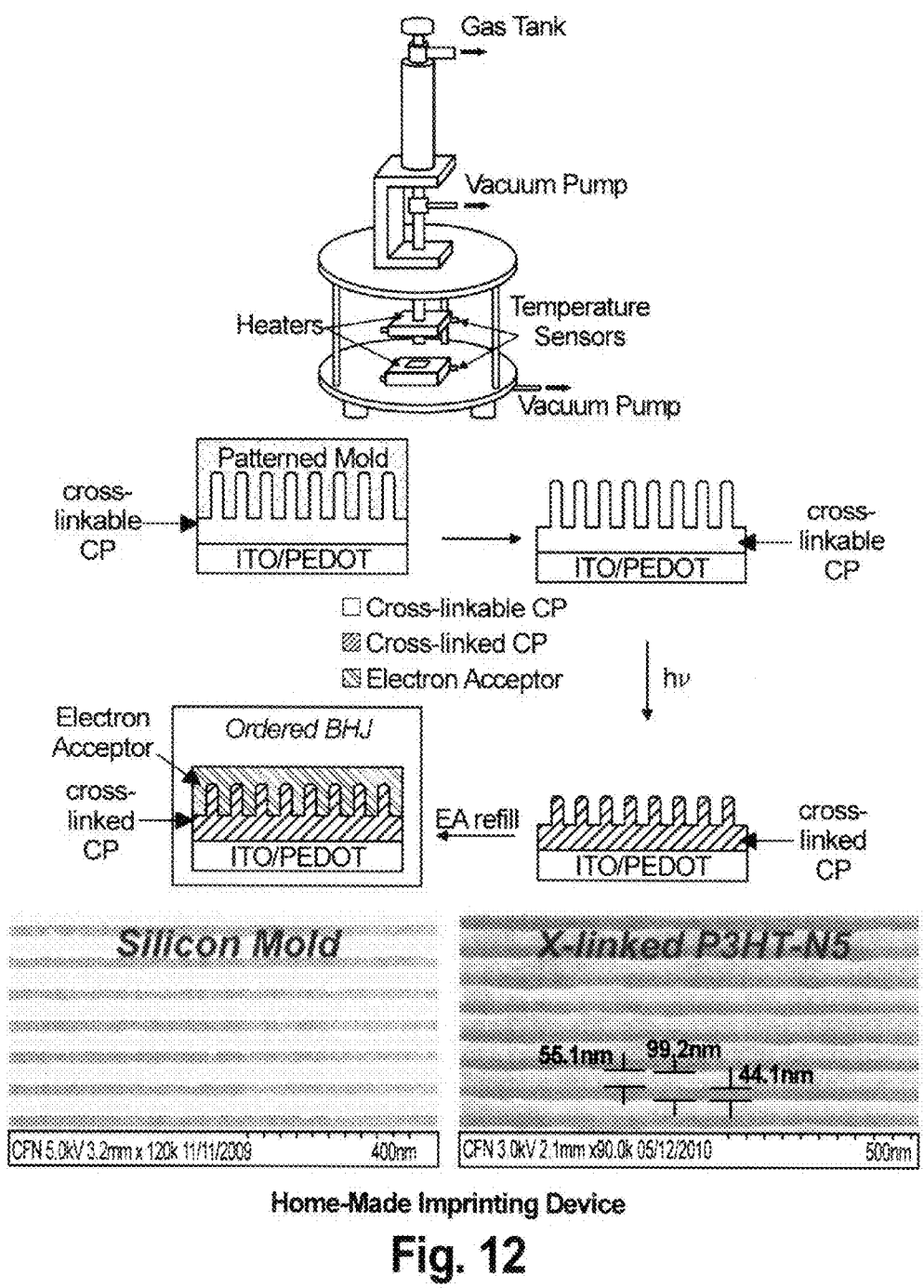
FIG. 12 is an illustration of a home-made imprinting device, a schematic representation of the preparation of an ordered bulk heterojunction (ordered BHJ), and scanning electron micrographs of the silicon mold (left side) and P3HT-N$_5$ film (right side), respectively.

In FIG. 12 a home-made imprinting device featuring a silicon mold was fabricated and used to imprint ("Patterned Mold") the non-crosslinked $P3HT-N_5$. After removal of the silicon mold, the imprinted structure was exposed to UV radiation. The scanning electron micrographs show the fidelity with which the mold pattern was transferred to the P3H T-$N_5$. The micrograph on the left shows the silicon mold used to imprint the $P3HT-N_5$ film shown on the right.

Figure 13:
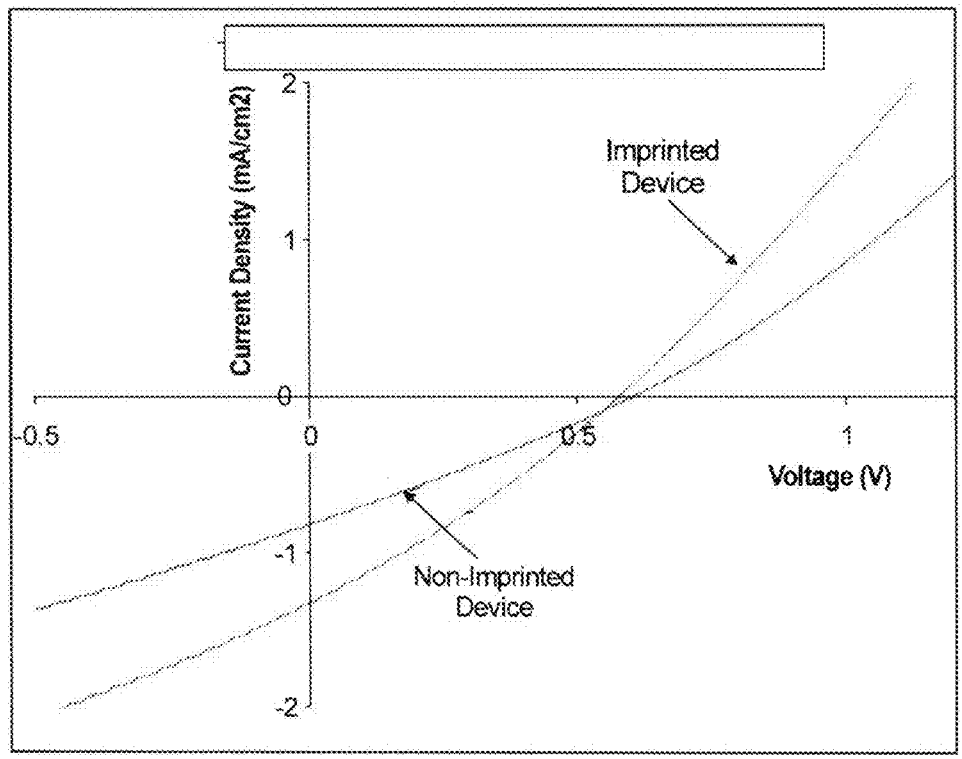
FIG. 13 is a graphic illustration of current density vs. voltage on an imprinted device and a non-imprinted device, and a chart with data representing the performance of devices with non-imprinted and imprinted P3HT-N$_5$.

FIG. 13 presents in chart form the performance of devices made by filling imprinted structures with PCBM used as the Electron acceptor (EA) material, and adding electrodes and comparing the devices made with non-imprinted and imprinted $P3HT-N_5$. There is a small but measurable improvement in properties for the imprinted devices as compared to the non-imprinted devices.

Figure 14:
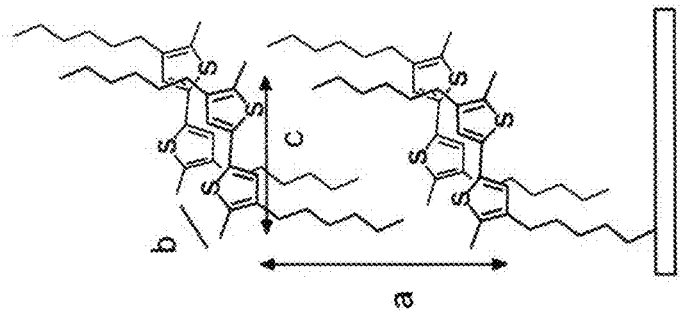
FIG. 14 is a chart presenting spacing data of the polymer structures as indicated by "a," "b," and "c," for the P3HT, P3HT-N$_5$ (non crosslinked), and P3HT-N$_5$ (crosslinked) polymers, Brinkmann, M.; Wittmann, J.-C. "Orientation of Regioregular Poly(3-hexylthiophene) by Directional Solidification: A Simple Method to Reveal the Semicrystalline Structure of a Conjugated Polymer," *Advanced Materials* 2006, 18, 860-863, the entire contents of which are incorporated herein by reference.

FIG. 14 presents in chart form GIXRD spacing data of the polymer structures as indicated by "a," "b," and "c," for the P3HT, $P3HT-N_5$ (non crosslinked), and $P3HT-N_5$ (crosslinked) polymers, respectively.

The (6-(3-thienyl)hexyloxy)-tert-butyldimethylsilane monomer, the silylether-protected Monomer 1, and $P3HT-Si_{mp}$ have been synthesized for the first time. This silylether protection strategy can be applied to the synthesis of other functional conjugated polymers. The reaction of converting hydroxy groups into azido functionalities has been demonstrated for the first time on a conjugated polymer for the preparation of $P3HT-N_{mp}$, which has also been synthesized for the first time, and whose azido loading percentage and molecular weight can be finely controlled. Compared with other crosslinking methods. UV-crosslinking $P3HT-N_{mp}$ does not involve additional small molecule crosslinkers, needs minimum loading percentage of azido groups (in principle, only two azido groups per polymer chain ensures full crosslinking), preferentially crosslinks alkyl chains without altering chain packing and electronic properties, and gives volatile $N_2$ as the only byproduct, eliminating introduction of small molecule impurities.

While the foregoing description has been made with reference to individual embodiments of the method, it should beunderstood that those skilled in the art, making use of the teaching herein, may propose various changes and modifications without departing from the method in its broader aspects. For example, it may be advantageous to synthesize a series of P3HT-$N_{mp}$ with different molecular weights and azido loading percentages in order to obtain the right combination for optimized UV exposure time. In other cases, P3HT-$N_{mp}$ may be used to build up ordered BHJ structures to improve OPV performance.

The description has not attempted to exhaustively enumerate all possible variations. That alternate embodiments may not have been presented for a specific portion of the invention, and may result from a different combination of described portions, or that other undescribed alternate embodiments may be available for a portion, is not to be considered a disclaimer of those alternate embodiments. It will be appreciated that many of those undescribed embodiments are within the literal scope of the following claims, and others are equivalent. The foregoing description being illustrative, the invention is limited only by the claims appended hereto.

The invention claimed is:
1. A polymer having the formula:

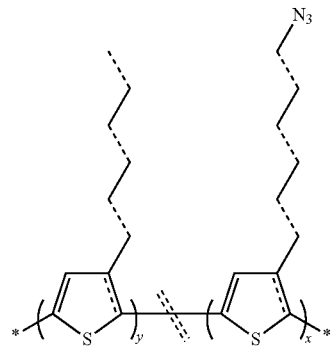

wherein x is between 1 and about 100 an y is between about 99 and about 1, and x+y=about 100.

2. A photovoltaic device comprising:
the polymer of claim 1 deposited and molded onto a substrate and
an electron-accepting material deposited on the polymer.

3. The photovoltaic device of claim 2, wherein the substrate comprises at least one of tin oxide, silicon, silicon dioxide, silicon nitride, glass, sapphire, or a metal.

4. The organic photovoltaic device of claim 2, wherein the substrate comprises tin oxide and poly(3,4-ethylenedioxythiophene).

* * * * *